United States Patent [19]

McKendry

[11] 4,108,629

[45] Aug. 22, 1978

[54] HERBICIDAL USE OF ESTERS OF AMINOHALOPYRIDYLOXY ACIDS

[75] Inventor: Lennon H. McKendry, Midland, Mich.

[73] Assignee: The Dow Chemical Company, Midland, Mich.

[21] Appl. No.: 745,714

[22] Filed: Dec. 1, 1976

Related U.S. Application Data

[60] Continuation-in-part of Ser. No. 342,782, Mar. 19, 1973, abandoned, which is a division of Ser. No. 166,308, Jul. 26, 1971, Pat. No. 3,755,339.

[51] Int. Cl.$^2$ .............................................. A01N 9/22
[52] U.S. Cl. ........................................................ 71/94
[58] Field of Search ........................................... 71/94

[56] References Cited

U.S. PATENT DOCUMENTS

| | | | |
|---|---|---|---|
| 2,341,868 | 2/1944 | Hitchcock et al. | 71/109 |
| 2,577,969 | 12/1951 | Jones | 71/109 |
| 3,276,856 | 10/1966 | Esposito | 71/94 |
| 3,285,925 | 11/1966 | Johnston et al. | 71/94 |
| 3,317,542 | 5/1967 | Haszeldine et al. | 71/94 |
| 3,317,549 | 5/1967 | Johnston | 71/94 |
| 3,483,246 | 12/1969 | Kaufman | 71/94 |
| 3,489,761 | 1/1970 | Kaver | 71/94 |
| 3,753,678 | 8/1973 | Young et al. | 71/94 |
| 3,883,541 | 5/1975 | Hamilton | 71/94 |

OTHER PUBLICATIONS

Cava, et al., "Pyridine Ders. II. Some Halogen, etc.;" (1958), J. Org. Chem. 23 pp. 1614–1616 (1958).
Veldstra, "Form and Function of Plant Growth Subs.", (1955), CA53, p. 18199 (1959).

*Primary Examiner*—Glennon R. Hollrah
*Attorney, Agent, or Firm*—S. Preston Jones; C. Kenneth Bjork

[57] ABSTRACT

Compounds corresponding to the formula

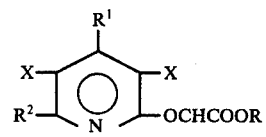

wherein X represents chloro, bromo, or fluoro; R represents alkyl of 1 to 12 carbon atoms or a radical having the formula —$(CH_2)_nOR^3$ wherein $n$ represents an integer of from 2 to 4 and $R^3$ represents lower alkyl of 1 to 4 carbon atoms or phenyl; M represents hydrogen or methyl; $R^1$ represents hydrogen, lower alkyl of 1 to 4 carbon atoms, amino or loweralkylamino of 1 to 4 carbon atoms; and $R^2$ represents hydrogen, X, loweralkyl, amino or loweralkylamino, with the proviso that one of $R^1$ or $R^2$ is always amino or loweralkylamino and the other of $R^1$ and $R^2$ is always other than amino or loweralkylamino are prepared. These compounds are useful as herbicides and as active agents in compositions used as herbicides.

8 Claims, No Drawings

HERBICIDAL USE OF ESTERS OF AMINOHALOPYRIDYLOXY ACIDS

CROSS-REFERENCE TO RELATED APPLICATION

This is a continuation-in-part of application Ser. No. 342,782, filed Mar. 19, 1973, now abandoned which in turn is a division of application Ser. No. 166,308, filed July 26, 1971, now U.S. Pat. No. 3,755,339, issued Aug. 28, 1973.

SUMMARY OF THE INVENTION

The present invention is directed to novel compounds corresponding to the formula

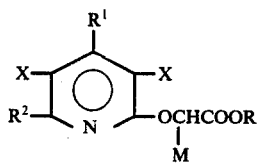

in this and succeeding formulae, wherein X represents chloro, bromo, or fluoro; R represents alkyl of 1 to 12 carbon atoms or a radical having the formula $-(CH_2)_nOR^3$ wherein $n$ represents an integer of from 2 to 4 and $R^3$ represents loweralkyl of 1 to 4 carbon atoms or phenyl; M represents hydrogen or methyl; $R^1$ represents hydrogen; loweralkyl of 1 to 4 carbon atoms, amino or loweralkylamino of 1 to 4 carbon atoms; and $R^2$ represents hydrogen, X, loweralkyl, amino or loweralkylamino, with the proviso that one of $R^1$ or $R^2$ is always amino or loweralkylamino and the other of $R^1$ and $R^2$ is always other than amino or loweralkylamino.

In the present specification and claims, the term "loweralkyl" is employed to designate a straight, branched or cyclic alkyl radical containing from 1 to 4 carbon atoms.

In the present specification and claims, the term "loweralkylamino" as employed designates either straight, branched chain or cyclic mono- or dialkylamino radicals wherein each alkyl group contains from 1 to 4 carbon atoms.

The present invention also is understood to encompass compounds wherein all the "X" substituents are the same as well as those wherein different halogens are present in the same compound.

For ease in understanding, it is to be understood that the term "amino" when used generally encompass compounds containing either an amino ($-NH_2$) radical or a loweralkylamino radical.

The present invention is also directed to plant husbandry and the raising of crops and is concerned with an agronomical practice and composition for improving the emergence, seed germination, seedling growth and harvest of crop plants. This invention also relates to herbicidal compositions and to methods of inhibiting or controlling undesirable plant growth therewith in the presence of important economic crops.

The active compounds of the present invention are crystalline solids or oils which are moderately soluble in common organic solvents.

The substituted aminohalopyridines of the present invention are prepared by the reaction of an aminohalopyridinol corresponding to the formula

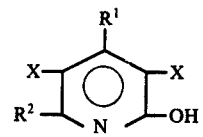

wherein $R^1$ and $R^2$ are as hereinbefore defined, with a halo-substituted loweralkyl ester of acetic acid or propionic acid corresponding to the formula

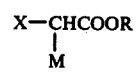

wherein M, R and X are as hereinbefore defined.

The reaction is initiated by contacting the reactants together in the presence of a reaction medium or solvent such as, for example, acetonitrile, dimethylformamide, p-dioxane, or dimethylsulfoxide and a base such as, for example, silver carbonate, potassium carbonate, sodium carbonate, sodium hydride or metallic sodium. The reaction is carried out at a temperature in the range of from about 25° to about 150° C, preferably at temperatures above 65° C. The reaction consumes the reactants in stoichiometric proportions, i.e., one equivalent of the pyridinol reactant per equivalent of the halo-ester reactant. However, due to the nature of the pyridyloxy ester formation, it is preferred that an excess of the halo-ester reactant be employed.

The base is employed in amounts ranging from about 1 to about 2 equivalents of base per equivalent of aminohalopyridinol reactant. The preferred amount is about 1 equivalent of base per equivalent of pyridinol reactant.

In carrying out the reaction, the reactants, reaction medium and catalyst are heated to the reaction temperature and maintained at this temperature in a state of agitation for a period of time of from about 0.5 to about 30 hours, until the reaction is complete. The reaction mixture is thereafter filtered with or without prior cooling. The solvent is thereafter removed by evaporation under reduced pressure. The product is purified by recrystallization from a solvent such as, for example, carbon tetrachloride, n-hexane, cyclohexane or a methanol-water mixture or by the use of combinations of these solvents and/or by the sequential use of one or more solvents.

In an alternative procedure, the substituted amino halopyridine compounds of the present invention wherein R is alkyl of 1 to 12 carbon atoms can be prepared by the reaction of an amino halopyridine corresponding to the formula

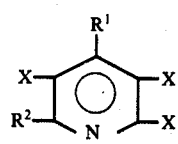

wherein X, $R^1$ and $R^2$ are as hereinbefore defined with an α-hydroxy acetic acid or propionic acid alkyl ester of the formula

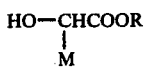

wherein M and R are as hereinbefore defined.

The reaction is initiated by contacting the reactants together in the presence of a reaction medium or solvent such as, for example, acetonitrile, dimethylformamide, p-dioxane, or dimethylsulfoxide and a base such as, for example, silver carbonate, potassium carbonate, sodium carbonate, sodium hydride or metallic sodium. The reaction is carried out at the reflux temperature of the mixture. The reaction consumes the reactants in stoichiometric proportions, i.e., one equivalent of the pyridine reactant per equivalent of the hydroxy acetic or propionic acid ester reactant. However, due to the nature of the pyridyloxy ester formation, it is preferred that an excess of the hydroxy acetic or propionic acid ester reactant be employed.

The base is employed in amounts ranging from about 1 to about 2 equivalents of base per equivalent of aminohalopyridine reactant.

In carrying out the reaction, the reactants, reaction medium and base are heated to the reflux temperature and maintained at this temperature and in a state of agitation for a period of time of from about 0.5 to about 10 hours or more, until the reaction is complete. The reaction mixture is thereafter cooled, diluted with water and extracted with a solvent such as dichloromethane or other conventional such solvents. The extract is dried, filtered and concentrated by heating under reduced pressure. The product is purified by the trituration with a solvent such as, for example, ether, n-hexane, cyclohexane, pentane or a pentane-ether mixture.

DESCRIPTION OF SOME PREFERRED EMBODIMENTS

The following examples illustrate the present invention and the manner by which it can be practiced but, as such, should not be construed as limitations upon the overall scope of the same.

EXAMPLE I:
4-Amino-3,5-dichloro-2-(pyridyloxy)acetic acid:ethyl ester

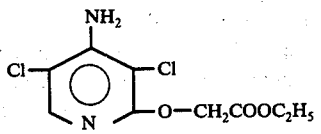

A mixture comprising 17.91 grams (0.1 mole) of 4-amino-3,5-dichloro-2-pyridinol, 12 milliliters (0.11 mole) of ethyl bromoacetate, 100 milliliters of acetonitrile and 27.5 grams (0.1 mole) of silver carbonate were heated at reflux for 5¼ hours. The hot solution was filtered and cooled. The residual solvent was removed therefrom by evaporation under reduced pressure. The crude reaction product was thereafter extracted twice with 50-milliliter portions of carbon tetrachloride; the carbon tetrachloride extracts were combined and the solvent evaporated under reduced pressure, the residue was thereafter recrystallized from n-hexane and 2 grams of the desired product was recovered. The product melted at 76.5°–78° C and was found by elemental analysis to have carbon, hydrogen, nitrogen and chlorine contents of 41.20, 3.89, 10.71 and 26.40 percent, respectively, as compared with the theoretical contents of 40.75, 3.77, 10.57 and 26.79 percent, respectively, calculated for the above-named structure.

EXAMPLE II:
4-Amino-3,5,6-trichloro-2-(pyridyloxy)acetic acid:ethyl ester

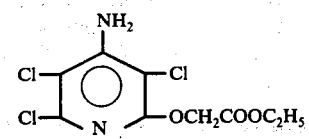

A mixture comprising ~4.2 grams (0.02 mole) of 4-amino-3,5,6-trichloro-2-pyridinol, 2.6 grams (0.02 mole) of potassium carbonate, 40 milliliters of acetonitrile and 3.2 milliliters (0.028 mole) of ethyl bromoacetate were heated under reflux for 2¾ hours. The mixture was cooled and filtered. The solvent was thereafter removed by evaporation under reduced pressure. The 4-amino-3,5,6-trichloro-2-(pyridyloxy)acetic acid:ethyl ester product was recovered in a yield of 3.85 grams (90.5 percent of theoretical) and melting at 96°–97° C. The product was found by elemental analysis to have carbon, hydrogen, nitrogen and chlorine contents of 36.4, 3.2, 9.4 and 34.8 percent, respectively, as compared with the theoretical contents of 38.1, 3.0, 9.4 and 35.5 percent, respectively, calculated for the above-named structure.

EXAMPLE III:
2-(3,5-Dichloro-6-fluoro-4-(methylamino)-2-pyridyloxy)propionic acid:ethyl ester

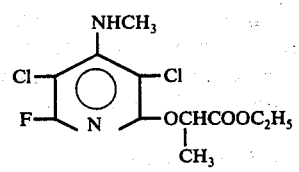

A mixture comprising 10.65 grams (0.05 mole) of 3,5-dichloro-2,6-difluoro-4-(methylamino)pyridine, 7.28 grams (0.07 mole) of ethyl glycolate and 150 milliliters of dry p-dioxane. To the mixture was added a dioxane slurry containing 3.6 grams (0.075 mole) of hexane washed sodium hydride (as a 50 percent oil dispersion). The mixture foamed and when foaming ceased, the mixture was heated under reflux (~100° C) for 2 hours. At the end of this period, the reaction mixture was poured into ice water and extracted 3 times with 100 milliliter portions of dichloromethane. The extracts were combined, dried, and filtered and thereafter concentrated under reduced pressure. The 2-(3,5-dichloro-6-fluoro-4-(methylamino)-2-pyridyloxy)propionic acid:ethyl ester product was recovered in a yield of 15 grams of a yellow oil. The product, in the form of a solid, was recovered by dissolving the oil in 100 milliliters of methylcyclohexane in a glass container and scratching the side of the container with a glass rod to precipitate the product. The product, melted at 67°–68.5° C and upon analysis, was found to have carbon, hydrogen and nitrogen contents of 42.61, 4.23 and 8.91 percent, respectively, as compared with the theoretical contents of 42.46, 4.21 and 9.0 percent, respectively, calculated for the above-named structure.

The following compounds of the present invention are prepared in accordance with the methods hereinbefore set forth.

4-Amino-3,5-dichloro-2-(pyridyloxy)acetic acid:methyl ester having a melting point of 119°–121° C;

4-Amino-3,5,6-trichloro-2-(pyridyloxy)acetic acid:2-butoxy ethyl ester having a molecular weight of 371.51;

2-[4-Methylamino-3,5,6-trichloro-2-(pyridyloxy)]propionic acid:n-octyl ester having a refractive index of 1.5231;

4-Amino-3,5-dichloro-2-(pyridyloxy)acetic acid:butyl ester having a melting point of 131°–133° C;

2-[4-Amino-3,5-dichloro-2-(pyridyloxy)]propionic acid:methyl ester having a molecular weight of 265.01;

6-Amino-3,5-dichloro-4-methyl-2-(pyridyloxy)acetic acid:methyl ester having a molecular weight of 265.01;

2-[6-Methylamino-3,5-dichloro-4-butyl-2-(pyridyloxy)]propionic acid:butyl ester having a molecular weight of 374.09;

2-[6-Dibutylamino-3,4,5-trichloro-2-(pyridyloxy)]propionic acid:ethyl ester having a molecular weight of 425.55;

4-Methylamino-3,5-dibromo-2-(pyridyloxy)acetic acid:4-methoxy butyl ester having a molecular weight of 333.05;

2-[6-Methylamino-3,5-difluoro-4-methyl-2-(pyridyloxy)]propionic acid:3-butoxy propyl ester having a molecular weight of 360.17;

2-[4-Amino-3,5-dichloro-2-(pyridyloxy)]propionic acid:ethyl ester having a melting point of 78°–83° C;

2-[4-Amino-3,5,6-trichloro-2-(pyridyloxy)]propionic acid:ethyl ester having a molecular weight of 313.48;

4-Amino-3,5,6-trichloro-2-(pyridyloxy)acetic acid:phenoxy methyl having a molecular weight of 377.52;

2-[6-Amino-3,5-dichloro-4-methyl-2-(pyridyloxy)]propionic acid:cyclopropyl ester having a molecular weight of 304.04;

2-[6-Cyclopropylamino-3,5-difluoro-4-butyl-2-(pyridyloxy)]propionic acid:cyclobutyl ester having a molecular weight of 327.16;

4-Amino-3,5-dichloro-6-fluoro-2-(pyridyloxy)acetic acid:ethyl ester having a melting point of 107.5°–109° C;

4-Amino-3,5-dichloro-6-fluoro-2-(pyridyloxy)acetic acid:methyl ester having a molecular weight of 270.01;

4-Methylamino-3,5-dichloro-6-fluoro-2-(pyridyloxy)acetic acid:ethyl ester having a melting point of 60°–60.2° C;

4-Dibutylamino-3,5,6-trifluoro-2-(pyridyloxy)acetic acid:butoxybutyl ester having a molecular weight of 462.56;

2-[4-Amino-3,5-dichloro-6-fluoro-2-(pyridyloxy)]propionic acid:ethyl ester having a melting point of 86°–88° C; and 2-[6-Isopropylamino-3,5-dichloro-4-propyl-2-(pyridyloxy)]propionic acid:isopropyl ester having a molecular weight of 377.09.

In accordance with the present invention, it has been discovered that the substituted aminohalopyridyloxy esters of the present invention are useful as herbicides. In accordance with this invention, a method for controlling or inhibiting the growth of undesirable plant species is provided which comprises applying to plants, plant parts or their habitat, an effective or growth inhibiting amount of at least one of the substituted aminohalopyridyloxy esters as set forth hereinabove.

An outstanding feature of the present invention is the ability of the ester compounds to control, either by post-emergent or pre-emergent application, the growth of small seeded grasses and broadleaf plants, such as, for example, barnyard grass, crabgrass, yellow foxtail, Johnson grass, wild oats, bindweed, pigweed, ragweed and wild mustard. This ability is of utmost importance since the compounds are not usually harmful to economical, large seeded crop plants, such as, for example, corn, rice, soybeans or wheat. This feature allows for selective control of the undesirable small seeded plants in the presence of the economical large seeded crop plants.

The application of the compounds of the present invention to plants and plant parts and their habitats, gives rise to varying degrees of response to the compounds depending upon the nature of the plant or seed, the stage of growth or maturity of the plant, the specific compound employed, and the dosage at which plant or plant part of habitat exposure to the compound is carried out, as well as environmental conditions. When large dosages of many of the compounds are applied to the foliage of undesirable plants, a substantially complete kill is obtained. Soil or foliar application of more dilute dosages of many of the compounds suppress the growth of the germinant seeds and seedlings of many undesirable grasses while having little or no effect upon the seeds, emerging seedlings or established plants of many desirable crop plants. Thus, many of the ester compounds can be employed for the selective control of emerging seedlings of undesirable weeds in plantings or stands of desirable crop plants.

The minimum amount of active compound applied should be that which is effective in controlling and/or killing undesirable plant growth. Ordinarily, for pre-emergent control, good results are obtained when from 0.01 to 50 pounds or more of at least one of the active aminohalopyridyloxy ester compounds are applied per acre. In foliage treatments, good results are obtained when from 0.1 to 200 pounds of active compound per acre are employed. In selective applications to foliage for the control of many undesirable weeds in the presence of desired crop plants, a uniform dosage of from about 1.0 to 75 pounds of active compound can be employed. In all selective applications, the exact dosage to be employed is dependent upon the resistance of the crop plant or their seeds to the ester compounds.

The present invention can be carried out by directly employing the ester compounds singly or in combination with each other. However, the present invention also embraces the employment of liquid, granular, encapsulated or dust compositions containing at least one of said compounds. In such usage, the compound or compounds can be modified with one or more of a plurality of chemically inert additaments or pesticidal materials including solvents or other liquid carriers, surface active dispersing agents or coarsely or finely divided inert solids. The augmented compositions are also adapted to be employed as concentrates and subsequently diluted with additional inert carrier, to produce other compositions in the form of dusts, sprays, granules, washes or drenches. In compositions where the additament is a coarsely or finely divided solid, a surface active agent or the combination of a surface active agent and a liquid additament, the added material cooperates with the active component so as to facilitate the invention. Whether the composition is employed in liquid form, as a wettable powder, or as a granular or encapsulated material, the active compound will normally be present in an amount of from about 5 to about 95 percent by weight of the total composition.

In the preparation of dust compositions, the toxicant products can be compounded with any of the finely divided solids, such as, for example, pyrophyllite, talc, chalk, gypsum, fuller's earth, bentonite, attapulgite, and the like. In such operations, the finely divided carrier is ground or mixed with the toxicant or wet with a solution of the toxicant in a volatile organic solvent. Also, such dust compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided clays, such as, for example, attapulgite, bentonite, diatomite, or the like.

Similarly, the toxicant products can be compounded with a suitable water-immiscible organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of water-immiscible solvent, emulsifying agent and water. Preferred dispersing agents which can be employed in these compositions, are oil-soluble materials including non-ionic emulsifiers such as, for example, the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable organic liquids which can be employed in the composition include, for example, petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an organic liquid such as, for example, acetone, methylene chloride, chlorobenzene and petroleum distillates. The preferred organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F at atmospheric pressure and having a flash point above 80° F. The proportion of the compounds of this invention employed in a suitable solvent may vary from about 2 to about 50 percent or higher.

In further embodiments, the compounds as employed in accordance with the present invention, or compositions containing the same, can be advantageously employed in the present invention in combination with one or more pesticidal or preservative compounds. In such embodiments, the pesticidal or preservative compound is employed either as a supplemental toxicant or as an additament. Representative operable pesticidal or preservative compounds include substituted phenols, cresols, substituted cresols and their metal salts, bisphenols and thiobisphenols; halogenated calicylanilides, organosulfur compounds, carbamate compounds, quaternary ammonium compounds, organometallic compounds, inorganic salts and miscellaneous other compounds, such as phenol, cresol, trichlorophenols, tetrachlorophenols, pentachlorophenol, p-chloro-m-cresol, sodium pentachlorophenol and other sodium, potassium, etc. salts of the phenols, substituted phenols, cresols and substituted cresols, di- and tri-brominated salicylanilides, 2,2'-methylenebis(3,4,6-trichlorophenol), 2,2'-thiobis(4,6-dichlorophenoxide), halogenated trifluoromethyl salicylanilide, disodium ethylenebisthiocarbamate, sodium N-methyldithiocarbamate, zinc dimethyldithiocarbamate, 2-mercaptobenzothiazole, 3,5-dimethyltetrahydro-1,3,5-2H-thiodiazine-2-thione, 2,3-dinitro-1,4-dithia-anthraquinone, dodecyl pyridinium chloride, alkyl dimethyl benzyl ammonium chloride, dialkyl dimethylammonium chloride, bis-tributyltin oxide, bis-tripropyltin oxide, copper pentachlorophenate, copper 8-hydroxyquinolate, sodium borate, 9-undecylenic acid, 10,10'-oxybisphenoxarsine, 1-(3-chloroallyl)-3,5,7-triaza-1-azonia-adamantane chloride, 1,4-bromobisacetobutene and substituted phosphorothioates (soil applied insecticides).

In application to an area to be treated, the compounds of this invention may be applied by spraying or by the use of mechanical spreaders in accordance with conventional practice. With respect to application, however, it will be noted that, depending upon the particular circumstances encountered, one method of application may be preferable over others. Thus, for example, for preferred pre-emergence application it has been found very satisfactory to apply the active compound in a liquid spray or on granules and incorporate it into the soil.

In a further method, the distribution can be accomplished by introducing a toxicant or toxicants into the water employed to irrigate the soil. In this method, the amount of water can be varied in accordance with the moisture equivalent or field capacity of the soil in order to obtain the desired depth of distribution of the toxicant.

The following embodiments are illustrative of the present methods.

EXAMPLE III

Forty-five parts by weight of one of the compounds 2-[4-amino-3,5-dichloro-6-fluoro-2-(pyridyloxy)]propionic acid:ethyl ester or 2-[4-dibutylamino-3,4,5-trichloro-2-(pyridyloxy)]propionic acid:ether ester is mixed and ground with 5 parts by weight of Triton X-155 surfactant (an alkylated aryl polyether alcohol) to prepare a water-dispersible concentrate composition containing 90 percent by weight of one of the ester compounds.

In a further operation, 25 parts by weight of 6-amino-3,5-dichloro-2-(pyridyloxy)acetic acid:methyl ester, 10 parts by weight of Triton X-155 surfactant and 65 parts by weight of xylene are mixed together to prepare an emulsifiable concentrate composition containing 25 percent by weight of said ester compound.

A mixture of 10 parts by weight of 2-[6-isopropyl-3,5-dichloro-4-propyl-2-(pyridyloxy)]propionic acid:isopropyl ester, 10 parts by weight of 2-[4-methylamino-3,5-dichloro-4-butyl-2-(pyridyloxy)]propionic acid:butyl ester, 0.1 part of Nacconol NR detergent (alkyl sulfonate), 0.1 part of Daxad No. 27 (a polymerized sodium salt of benzoid alkyl sulfonic acids) and 200 parts of water are ball-milled together to prepare a water dispersible liquid concentrate composition containing 20 parts by weight of the mixed pyridine compounds. The concentrate compositions thus prepared can be dispersed in water to prepare aqueous composition which have very desirable wetting and penetrating properties and are adpated to distribute growth inhibiting amounts of the pyridine compound on plant parts.

EXAMPLE IV

In separate operations, aqueous compositions containing aminohalopyridyloxy ester compounds are prepared as follows:

Four parts by weight of one of the ester compounds, 0.08 part of sorbitan trioleate (Span 85), and 0.02 part of a sorbitan monoleate polyoxyethylene derivative (Tween 80) are dispersed in 40 milliliters of acetone to produce a concentrate composition in the form of a water-soluble liquid containing one of the ester compounds as the sole active agent. The compounds employed in these procedures include the following:

4-Amino-3,5-dichloro-2-(pyridyloxy)acetic acid:methyl ester;

2-[4-Amino-3,5-dichloro-2-(pyridyloxy)]propionic acid:methyl ester;

4-Amino-3,5-dichloro-2-(pyridyloxy)acetic acid:ethyl ester;

4-Amino-3,5,6-trichloro-2-(pyridyloxy)acetic acid:ethyl ester;

2-(3,5-Dichloro-6-fluoro-4-(methylamino)-2-pyridyloxy)propionic acid:ethyl ester;

2-[4-Amino-3,5-dichloro-6-fluoro-2-(pyridyloxy)]-propionic acid:ethyl ester;

4-Amino-3,5-dichloro-6-fluoro-2-(pyridyloxy)acetic acid:ethyl ester;

4-Dibutylamino-3,5,6-trifluoro-2-(pyridyloxy)acetic acid:butoxybutyl ester;

4-Amino-3,5-dichloro-6-fluoro-2-(pyridyloxy)acetic acid:methyl ester;

4-Methylamino-3,5-dichloro-6-fluoro-2-(pyridyloxy)acetic acid:ethyl ester;

2-[4-Methylamino-3,5,6-trichloro-2-(pyridyloxy)]-propionic acid:n-octyl ester;

2-[4-Methylamino-3,5-dichloro-4-butyl-2-(pyridyloxy)]propionic acid:butyl ester;

4-Amino-3,5-dichloro-2-(pyridyloxy)acetic acid:butyl ester;

4-Amino-3,5,6-trichloro-2-(pyridyloxy)acetic acid:2-butoxy ethyl ester;

2-[6-Amino-3,5-dichloro-4-methyl-2-(pyridyloxy)]acetic acid:methyl ester;

2-[6-Dibutylamino-3,4,5-trichloro-2-(pyridyloxy)]-propionic acid:ethyl ester;

4-Methylamino-3,5-dibromo-2-(pyridyloxy)acetic acid:4-methoxy butyl ester;

2-[6-Methylamino-3,5-difluoro-4-methyl-2-(pyridyloxy)]propionic acid:3-butoxy propyl ester;

4-Amino-3,5-dichloro-2-(pyridyloxy)propionic acid:ethyl ester; and

2-[6-Isopropylamino-3,5-dichloro-4-propyl-2-(pyridyloxy)]propionic acid:isopropyl ester.

Portions of these concentrate compositions are dispersed in separate portions of water to provide aqueous compositions, each containing 0.44 pound of one of the ester compounds per 100 gallons of ultimate aqueous mixture. The diluted compositions have very desirable wetting and penetrating properties and are adapted to distribute growth inhibiting amounts of the ester compound on plant parts.

EXAMPLE V

Representative products of the present invention were evaluated for the post-emergent control of barnyard grass, wild mustard, crabgrass, pigweed, yellow foxtail and bindweed. In these evaluations, plots of the above plant species growth to a height of about 4 inches were used. Aqueous spray compositions, each containing 4,000 parts of a given aminohalopyridyloxy ester compound per million parts of ultimate composition, were prepared in accordance with the procedures of Example IV, and each separate composition was applied to a separate plot. The application was made to the point of run-off and was carried out with conventional spraying equipment. Other plots were sprayed with similar compositions containing no toxicant to serve as controls. Thereafter the plots were maintained under conditions conducive for plant growth. Two weeks after treatment, the plots were examined for plant growth and evaluated. The results of the examination of the treated plots are set forth below in Table A.

TABLE A

| Compound Employed | Percent Kill and Control of | | | | | |
|---|---|---|---|---|---|---|
| | Barnyard Grass | Wild Mustard | Crabgrass | Pigweed | Yellow Foxtail | Bindweed |
| 4-Amino-3,5-dichloro-2-(pyridyloxy)-acetic acid:ethyl ester | 95 | 90 | 100 | 100 | 70 | 100 |
| 4-Amino-3,5,6-trichloro-2-(pyridyloxy)acetic acid:ethyl ester | 80 | 95 | 90 | 100 | 80 | 100 |
| 4-Amino-3,5-dichloro-2-(pyridyloxy)-acetic acid:butyl ester | 85 | 95 | 95 | 100 | 80 | 75 |
| 4-Amino-3,5-dichloro-2-(pyridyloxy)-acetic acid:methyl ester | 100 | 100 | 100 | 100 | 100 | 100 |
| 2-[4-Amino-3,5-dichloro-2-(pyridyloxy)]propionic acid:ethyl ester | 100 | 95 | 100 | 100 | 100 | 100 |
| Control | 0 | 0 | 0 | 0 | 0 | 0 |

EXAMPLE VI

Representative products of the present invention were evaluated for the post-emergent control of barnyard grass, annual morning glory, crabgrass, Jimson weed, yellow foxtail, cocklebur and Johnson Grass. In these evaluations, plots of the above plant species' growth to a height of about 4 inches were used. Aqueous spray compositions, each containing 2,000 parts of a given aminohalopyridyloxy ester compound per million parts of ultimate composition, were prepared in accordance with the procedures of Example IV, and each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated. The results of the examination of the treated plots are set forth below in Table B.

TABLE B

| Compound Employed | Percent Kill and Control of | | | | | | |
|---|---|---|---|---|---|---|---|
| | Barnyard Grass | Annual Morning Glory | Crabgrass | Cocklebur | Yellow Foxtail | Johnson Grass | Jimson Weed |
| 2-[4-Methylamino-3,5,6-trichloro-2-(pyridyloxy)]propionic acid:n-octyl ester | 90 | 90 | 99 | 100 | 98 | 95 | 95 |
| 4-Amino-3,5-dichloro-6-fluoro-2-(pyridyloxy)acetic acid:ethyl ester | 50 | 100 | 80 | 100 | 95 | 35 | 100 |
| 4-Methylamino-3,5-dichloro-6-fluoro-2-(pyridyloxy)acetic acid:ethyl ester | 70 | 100 | 100 | 100 | 95 | 90 | 100 |
| 2-[4-methylamino-3,5-dichloro-6-fluoro-2-(pyridyloxy)]-propionic acid:ethyl ester | 98 | 100 | 98 | 100 | 100 | 98 | 98 |
| 2-[4-Amino-3,5-dichloro-6-fluoro-2-(pyridyloxy)]propionic acid:ethyl ester | 90 | 100 | 100 | 100 | 95 | 100 | 100 |

EXAMPLE VII

Aqueous compositions of various ester compounds prepared in accordance with Example IV were employed for pre-emergent applications on plots immediately after they were seeded with crabgrass, wild oats, barnyard grass, wild mustard, pigweed, yellow foxtail and bindweed. Other plots similarly seeded with the above plant species were treated with like compositions containing no toxicant to serve as control plots. The treating applications were carried out by drenching the soil with the aqueous compositions to obtain a treating rate of 20 pounds per acre. Thereafter, the plots were maintained under conditions conducive for good plant growth. Two weeks after treatment, the plots were examined to determine the percent plant growth and evaluated. The results of the examinations are set forth below in Table C.

TABLE C

| Compound Employed | Percent Kill and Control of | | | | | | |
|---|---|---|---|---|---|---|---|
| | Barnyard Grass | Wild Mustard | Crabgrass | Pigweed | Yellow Foxtail | Bindweed | Wild Oats |
| 4-Amino-3,5-dichloro-2-(pyridyloxy)acetic acid:ethyl ester | 100 | 100 | 100 | 100 | 100 | 100 | 90 |
| 4-Amino-3,5,6-trichloro-2-(pyridyloxy)acetic acid:ethyl ester | 100 | 100 | 100 | 100 | 100 | 100 | 80 |
| 4-Amino-3,5-dichloro-2-(pyridyloxy)acetic acid:butyl ester | 100 | 100 | 100 | 100 | 100 | 100 | 95 |
| 4-Amino-3,5-dichloro-2-(pyridyloxy)acetic acid:methyl ester | 100 | 100 | 100 | 100 | 100 | 100 | 95 |
| 2-[4-Amino-3,5-dichloro-2-(pyridyloxy)]propionic acid:ethyl ester | 100 | 100 | 100 | 100 | 100 | 100 | 95 |
| Control | 0 | 0 | 0 | 0 | 0 | 0 | 0 |

EXAMPLE VIII

Aqueous compositions of various ester compounds prepared in accordance with Example IV were employed for pre-emergent applications on plots immediately after they were seeded with crabgrass, annual morning glory, barnyard grass, Jimson weed, pigweed, yellow foxtail and Johnson grass. Other plots similarly seeded with the above plant species were treated with like compositions containing no toxicant to serve as control plots. The treating application were carried out by drenching the soil with the aqueous compositions to obtain a treating rate of 4 pounds per acre. Thereafter, the plots were maintained under conditions conductive for good plant growth. Two weeks after treatment, the plots were examined to determine the percent plant growth and evaluated. The results of the examinations are set forth below in Table D.

TABLE D

| Compound Employed | Percent Kill and Control of | | | | | | |
|---|---|---|---|---|---|---|---|
| | Barnyard Grass | Annual Morning Glory | Crabgrass | Pigweed | Yellow Foxtail | Johnson Grass | Jimson Weed |
| 4-Amino-3,5-dichloro-6-fluoro 2-(pyridyloxy)acetic acid:ethyl ester | 99 | 100 | 100 | 100 | 85 | 80 | 100 |
| 4-Methylamino-3,5-dichloro-6-fluoro-2-(pyridyloxy)acetic acid:ethyl ester | 90 | 100 | 100 | 100 | 100 | 99 | 100 |
| 2-[4-Methylamino-3,5-dichloro-6-fluoro-2-(pyridyloxy)]propionic acid-ethyl ester | 100 | 80 | 100 | 100 | 100 | 100 | 100 |
| 2-[4-Amino-3,5-dichloro-6-fluoro-2-(pyridyloxy)]propionic acid-ethyl ester | 99 | 100 | 99 | 100 | 99 | 100 | 100 |

EXAMPLE IX

2-[4-Amino-3,5-dichloro-2-(pyridyloxy)]propionic acid:ethyl ester was employed for the selective control of emerging seedlings of the weed plants, barnyard grass, yellow foxtail, Johnson grass, pigweed, ragweed and mild mustard in plots seeded with the above-named plant species and the crop plant wheat. The plots were treated with aqueous compositions prepared as set forth in Example IV containing the above-named compound as the sole toxicant therein. Other plots similarly seeded with the above-named plant species were treated with aqueous compositions containing no toxicant to serve as control plots. The treating applications were carried out by drenching the soil with the aqueous compositions to obtain a treating rate of 1 pound per acre. Thereafter, the plots were maintained under conditions conductive to good plant growth. Examination of the plots two weeks after treatment showed substantially complete kill and control of all of the weed plant species and profuse growth of wheat. In the control plots, no kill or control of any of the plant species could be ascertained.

EXAMPLE X

4-Amino-3,5-dichloro-2-(pyridyloxy)acetic acid:butyl ester was evaluated for the selective post-emergent control of wild oats, Johnson grass, wild mustard, pigweed, bindweed, barnyard grass and yellow foxtail in plots containing these plants species and soybean plants. In this evaluation, the plants were of a height of about 4 inches. An aqueous spray composition containing 4,000 parts of the compound per million parts of ultimate composition and prepared in accordance with the procedures of Example IV, as applied to a plot containing the above plant species. The application was made to the point of run-off employing conventional spraying equipment. Other plots containing the same plant species were treated with compositions containing no toxicant, to serve as controls. Thereafter, the plots were held for a period of two weeks under conditions conducive for good plant growth. At the end of this period, the plots were examined to determine the degree of kill and control of the plants. In the control plots, all of the plants were growing rapidly and no kill or control of any of the plants could be found. In the ester treated plot, there was substantially complete kill and control of wild oats, Johnson grass, wild mustard, pigweed, bindweed, barnyard grass and yellow foxtail and no injury could be found to the soybean plants which were thriving and growing profusely.

PREPARATION OF STARTING MATERIALS

The 4- and 6-amino-(di- or tri-)halo-2-pyridinols employed as starting materials can be prepared by reacting an appropriate 4- or 6-amino-tri- or tetrahalopyridine, containing a halogen atom in the 2-position with an aqueous solution of an alkali metal hydroxide at a temperature of from about 120° to about 200° C.

What is claimed is:

1. A method for controlling the growth of undesirable plant species which comprises applying to plants, plant parts of their habitats a herbicidally effective amount of a compound corresponding to the formula

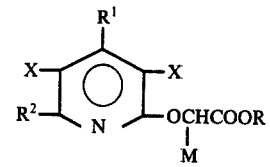

wherein X represents chloro or bromo; R represents alkyl of 1 to 12 carbon atoms or a radical having the formula $-(CH_2)_nOR^3$ wherein $n$ represents an integer of from 2 to 4 and $R_3$ represents lower alkyl of 1 to 4 carbon atoms or phenyl; M represents hydrogen or methyl; $R^1$ represents hydrogen, loweralkyl of 1 to 4 carbon atoms, amino or loweralkylamino of 1 to 4 carbon atoms; and $R^2$ represents hydrogen, X, loweralkyl, amino or loweralkylamino, with the proviso that one of $R^1$ or $R^2$ is always amino or loweralkylamino and the other of $R^1$ and $R^2$ is always other than amino or loweralkylamino.

2. The method of claim 1 wherein the compound is 4-amino-3,5-dichloro-2-(pyridyloxy)acetic acid:ethyl ester.

3. The method of claim 1 wherein the compound is 4-amino-3,5-dichloro-2-(pyridyloxy)acetic acid:butyl ester.

4. The method of claim 1 wherein the compound is 4-amino-3,5-dichloro-2-(pyridyloxy)acetic acid:methyl ester.

5. The method of claim 1 wherein the compound is 2-[4-amino-3,5-dichloro-2-(pyridyloxy)]propionic acid:ethyl ester.

6. The method of claim 1 wherein the compound is 4-amino-3,5,6-trichloro-2-(pyridyloxy)acetic acid:ethyl ester.

7. A composition for the control of undesirable plant growth which comprises as the active agent a herbicidally effective amount of a compound corresponding to the formula

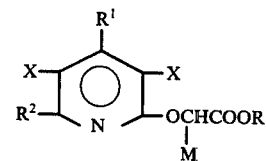

wherein X represents chloro or bromo; R represents alkyl of 1 to 12 carbon atoms or a radical having the formula $-(CH_2)_nOR^3$ wherein $n$ represents an integer of from 2 to 4 and $R_3$ represents lower alkyl of 1 to 4 carbon atoms or phenyl; M represents hydrogen or methyl; $R^1$ represents hydrogen, loweralkyl of 1 to 4 carbon atoms, amino or loweralkylamino of 1 to 4 carbon atoms, and $R^2$ represents hydrogen, X, loweralkyl, amino or loweralkylamino, with the proviso that one of $R^1$ or $R^2$ is always amino or loweralkylamino and the other of $R^1$ and $R^2$ is always other than amino or loweralkylamino in admixture with a chemically inert solid or liquid carrier therefor.

8. The composition of claim 7 wherein the active agent constitutes from about 5 to about 95 percent by weight of the total composition.

* * * * *

UNITED STATES PATENT AND TRADEMARK OFFICE
CERTIFICATE OF CORRECTION

PATENT NO. : 4,108,629
DATED : August 22, 1978
INVENTOR(S) : Lennon H. McKendry

It is certified that error appears in the above-identified patent and that said Letters Patent are hereby corrected as shown below:

Column 12, line 27, "conductive" should read
-- conducive --;

Column 13, line 10, "conductive" should read
-- conducive --;

Column 13, line 25, "plants" (1st occurrence) should read -- plant --.

Column 13, line 30, "as applied" should read -- was applied --

Column 13, line 64, "of their" should read -- or their -- ;

Column 14, line 12, "$R_3$" should read -- $R^3$ --;

Column 14, line 51, "$R_3$" should read -- $R^3$ --

Signed and Sealed this

Twelfth Day of June 1979

[SEAL]

Attest:

RUTH C. MASON
Attesting Officer

DONALD W. BANNER
Commissioner of Patents and Trademarks